United States Patent [19]
Nutt

[11] 4,102,877
[45] Jul. 25, 1978

[54] CYCLIZATION OF PEPTIDES

[75] Inventor: Ruth F. Nutt, Green Lane, Pa.

[73] Assignee: Merck & Co., Inc., Rahway, N.J.

[21] Appl. No.: 709,568

[22] Filed: Jul. 28, 1976

[51] Int. Cl.² .......................................... C07C 103/52
[52] U.S. Cl. ........................................... 260/112.5 R
[58] Field of Search .................. 260/112.5 R; 424/177

[56] References Cited

U.S. PATENT DOCUMENTS

| 3,705,887 | 12/1972 | Wieland et al. | 260/112.5 R |
| 3,719,656 | 3/1973 | Jolles | 260/112.5 R |
| 3,753,970 | 8/1973 | Bouchaudon et al. | 260/112.5 R |

FOREIGN PATENT DOCUMENTS

| 372,681 | 10/1963 | Switzerland | 260/112.5 R |

OTHER PUBLICATIONS

Ned M. Wernshenker, et al., Tet. Let. 32, pp. 3281-3284 (1972).
Von R. Schwyer, et al., Hel. Chim. Acta. 40, 1957, pp. 624-639.
Motonori Ohno, et al., J. Am. Chem. Soc. 93, 1971, pp. 5251-5254.

*Primary Examiner*—Delbert R. Phillips
*Attorney, Agent, or Firm*—Walter Patton

[57] ABSTRACT

The invention disclosed herein relates to the novel method for the preparation of cyclic peptides, wherein a linear peptide is reacted, in solution in a polar organic solvent, with an insoluble, resin-bound carboxyl-activating reagent such as resin-bound isopropylcarbodiimide. Cyclic peptides thus obtained have been found to retain biological activity characteristic of their linear counterparts, with increased biostability; the cyclic peptide, Gramicidin S, which can be prepared by this method, is a valuable antibacterial.

1 Claim, No Drawings

CYCLIZATION OF PEPTIDES

This invention is concerned generally with a novel process generally applicable for the preparation of cyclic peptides, wherein a linear peptide is reacted, in solution in a substantially anhydrous polar organic solvent, with an insoluble resin-bound carboxyl-activating reagent, preferably isopropylcarbodiimide bound to a methylated cross-linked polystyrene resin support. In this process, the resin-bound isopropylcarbodiimide reacts with the peptide to form a resin-bound linear peptide intermediate in which the C-terminal carboxyl group of the linear peptide is activated, whereupon the linear peptide undergoes cyclization and is released from the insoluble resin support to form a solution of the cyclic peptide substantially free from by-products formed in the reaction, said by-products remaining bound to the insoluble resin support. These by-products are rapidly, and substantially quantitatively, removed from the reaction mixture by filtration, and the cyclic peptide is readily recovered from the filtered solution in substantially pure form. Biologically active linear peptides are converted, in accordance with this peptide-cyclizing process to corresponding cyclic peptides which retain biological activity, together with increased stability particularly towards enzyme degradation.

The abbreviated designations, which are used herein for the amino acid components, their derivatives, and certain preferred protecting groups employed in this invention are as follows:

| Amino Acids | Abbreviated Designation |
|---|---|
| L-alanine | L-ala |
| glycine | gly |
| D-leucine | D-leu |
| L-leucine | L-leu |
| L-lysine | L-lys |
| L-ornithine | L-orn |
| D-phenylalanine | D-phe |
| L-phenylalanine | L-phe |
| L-proline | L-pro |
| L-valine | L-val |

| Derivatives: Protecting Groups | Abbreviated Designation |
|---|---|
| Toluenesulfonyl | tos |
| Triphenylmethyl | trityl |

In accordance with the presently invented peptide-cyclizing process, a linear peptide, such as the hexapeptide L-leu-gly-L-pro-L-phe-L-ala-gly, the protected decapeptide L-val-(tos)-L-orn-L-leu-D-phe-L-pro-L-val-(tos)-L-orn-L-leu-D-phe-L-pro, and the like (in which functional groupings, and particularly strongly-basic amino groups, which may be reactive under the conditions of this cyclizing process, are protected by acyl-type amino-protecting groups such as trifluoroacetyl, toluene-sulfonyl, and the like), is dissolved in an anhydrous polar organic solvent, such as dimethylformamide, or mixtures of anhydrous polar and non-polar solvents such as dimethyl-formamide:methylenechloride, and the like. A resin-bound carboxyl-activating reagent, such as resin-bound isopropyl-carbodiimide, preferably about 1-15 parts of resin-bound carboxyl-activating reagent to one part of linear peptide, is suspended in the solution, and a base, such as triethylamine, is added in an amount sufficient to adjust the pH of the suspension within the range of about 6-8; if desired, a catalyst, such as hydroxybenzotriazole, may be added. The peptide-cyclizing reaction is ordinarily conducted by stirring the suspension at a temperature of about 25° C. for a period of about 15 to 36 hours, although higher or lower reaction temperatures and correspondingly shorter or longer reaction periods may be employed, if desired. The reaction mixture is filtered, thereby removing the insoluble resin-support together with the by-products (such as isopropylurea) which result from the reaction and which remain bound on the resin support. Following filtration, the insoluble resin is washed with dimethylformamide, and the combined filtrate and washings are evaporated in vacuo to give the cyclic peptide such as cyclo-(L-leu-gly-L-pro-L-phe-L-ala-gly),cyclo-(L-val-(tos)-L-orn-L-leu-D-phe-L-pro)$_2$, and the like. Where the cyclic peptide contains protected functional groupings, the unprotected cyclic peptide is conveniently obtained by reacting the protected derivative with sodium in liquid ammonia, thereby forming the unprotected cyclic peptide such as cyclo-(L-val-L-orn-L-leu-D-phe-L-pro-L-val-L-orn-L-leu-D-phe-L-pro); the latter is conveniently converted to the hydrochloride by dissolving the unprotected cyclic peptide in dilute aqueous hydrochloric acid solution. Sufficient ethanol is added to this solution to completely precipitate the cyclic peptide hydrochloride, and the precipitated material is recovered by filtration and dried to give the cyclic peptide hydrochloride, such as cyclo-(L-val-L-orn-L-leu-D-phe-L-pro)$_2$ dihydrochloride, in substantially pure form.

The following examples illustrate methods of carrying out the present invention but it is to be understood that these examples are given for purposes of illustration and not of limitation.

EXAMPLE 1

About 28 mg. of L-leu-gly-L-pro-L-phe-L-ala-gly is dissolved in 15 ml. of purified dimethylformamide, and to the solution is added 100 mg. of resin-bound isopropylcarbodiimide and about 0.05 ml. of triethylamine. The resulting mixture is stirred at room temperature for about 15 hours, an additional 500 mg. of resin-bound isopropylcarbodiimide is added, and the mixture is stirred at room temperature for an additional 24-hour period. The reaction mixture is filtered, the insoluble resin and by-products are washed with dimethylformamide, and the combined filtrate and washings are analyzed by thin layer chromatography, which shows conversion of the linear hexapeptide to cyclo-(L-leu-gly-L-pro-L-phe-L-ala-gly).

EXAMPLE 2

About 15.65 mg. of L-leu-gly-L-pro-L-phe-L-ala-gly is dissolved in a mixture of 0.15 ml. of dimethylformamide and 0.45 ml. of methylene chloride; about 1 μl. of triethylamine is added thereby adjusting the pH of the solution to a pH of about 7.2. To the resulting solution is then added approximately 200 mg. of polystyrene resin-bound isopropyldicarbodiimide, followed by an additional 0.4 ml. of methylene chloride. The resulting suspension is stirred at room temperature for a period of about 18 hours. The reaction mixture is filtered thereby removing the insoluble resin and by-products; thin layer chromatography of the filtered solution shows that substantially all of the linear hexapeptide has been converted to cyclo-(L-leu-gly-L-pro-L-phe-L-ala-gly).

EXAMPLE 3

About 500 mg. of trityl-(L-val-(tos)-L-orn-L-leu-D-phe-L-pro)₂OH is dissolved in 12 ml. ethyl acetate, the solution is cooled to about 0° C., and the solution is maintained at 0° C. while hydrogen chloride gas is passed through the solution for about 5 minutes followed by nitrogen gas for about 5 minutes. About 50 ml. of a mixture of petroleum ether:ether (2:1) is added to the reaction solution with stirring, and the material which precipitates is recovered by filtration and dried to give approximately 450 mg. of the decapeptide hydrochloride, HCl.(L-val-(tos)-L-orn-L-leu-D-phe-L-pro)₂OH. About 450 mg. of resin-bound isopropylcarbodiimide, moist with dimethylformamide, is added to a solution containing 450 mg. of HCl.(L-val-(tos)-L-orn-L-leu-D-phe-L-pro)₂OH, 2 ml. dimethylformamide, 45 μl. of triethylamine and 100 mg. hydroxybenzotriazole catalyst, and the resulting suspension is stirred at room temperature for a period of about 24 hours. The insoluble resin and by-products are removed by filtration, washed with dimethylformamide, and the solvent is evaporated from the combined filtrate and washings in vacuo. The residual material is triturated with water to give 200 mg. of cyclo-(L-val-(tos)-L-orn-L-leu-D-phe-L-pro)₂.

About 140 mg. of cyclo-(L-val-(tos)-L-orn-L-leu-D-phe-L-pro)₂ are suspended in 80 ml. of liquid ammonia, and small pieces of metallic sodium are added, portionwise with stirring, to this suspension until the blue color, which forms on addition of the sodium, remains; ammonium chloride is then added to the suspension in an amount merely sufficient to convert the excess sodium to sodium chloride. The reaction mixture is warmed to room temperature, thereby evaporating the liquid ammonia, and the residual material is dissolved in a small amount of 1N aqueous hydrochloric acid solution. To this solution is added sufficient ethanol to completely precipitate the hydrochloride, which is recovered by filtration, dried and recrystallized from a mixture of 1N aqueous hydrochloric acid:ethanol (1:1) to give about 100 mg. of cyclo-(L-val-L-orn-L-leu-D-phe-L-pro)₂dihydrochloride, also referred to as Gramicidin S dihydrochloride; m.p. 278°–279° C., dec.

The resin-bound isopropylcarbodiimide, utilized in the procedures described in Examples 1-3 hereinabove, is prepared as follows: A mixture of 31.8 grams of potassium phthalimide, 25 grams of chloromethylated polystyrene resin (having 2% cross-linking and containing 2.75 milliequivalents of chlorine per gram of resin) and 250 ml. dimethylformamide is stirred at 100° C. for 5.5 hours. The mixture is cooled, filtered, and the insoluble resin product is washed with dimethylformamide, water, and ether, and dried to give 29 grams of resin-bound phthalimide.

A mixture of twenty-six grams of resin-bound phthalimide, 26 ml. of 95% aqueous hydrazine, and 100 ml. ethanol is heated under reflux with stirring for 5 minutes, whereupon some solid material precipitates, and an additional 200 ml. of ethanol is added; and the resulting mixture is heated under reflux with stirring for an additional 4.5 hours. The reaction mixture is cooled, filtered, and the precipitated material is washed with ethanol, water, methylene chloride and tetrahydrofuran, and dried to give 26 grams of the corresponding aminomethylated polystyrene resin.

A mixture of about 20 grams of this aminomethylated polystyrene resin, 110 ml. tetrahydrofuran and 10 grams of isopropylisocyanate is stirred at room temperature for approximately 16 hours, and the insoluble resin material is recovered by filtration, washed with tetrahydrofuran, methanol and methylene chloride, and dried to give about 21 grams of resin-bound isopropylurea.

A mixture of 5 grams of resin-bound isopropylurea, 25 ml. of methylene chloride, 5.26 grams tosyl chloride and 4.0 ml. of triethylamine is stirred at reflux temperature for about 15 hours. The reaction mixture is cooled, filtered, and the insoluble resin product is washed with four 50 ml.-portions of methylene chloride, and dried to give approximately 5.0 grams resin-bound isopropylcarbodiimide.

Various changes and modifications may be made in carrying out the present invention without departing from the spirit and scope thereof. In addition to the particular linear peptides, the resin-bound isopropylcarbodiimide and dimethylformamide solvent utilized in the procedures particularly described hereinabove, one skilled in the art would appreciate that other linear peptides and protected derivatives thereof, other insoluble resin-bound carboxyl-activating agents, and other polar organic reaction solvents may be employed in the practice of the herein-invented peptide-cyclizing process.

What is claimed is:

1. The process which comprises dissolving one part of a peptide, selected from the group consisting of the linear hexapeptide L-leu-gly-L-pro-L-phe-L-ala-gly, and the protected linear decapeptide L-val-(tos)-L-orn-L-leu-D-phe-L-pro-L-val-(tos)-L-orn-L-leu-D-phe-L-pro in a substantially anhydrous polar organic solvent comprising dimethylformamide adjusted to a pH of about 6–8 with triethylamine; suspending in this solution about one to fifteen parts of isopropylcarbodiimide bound to an insoluble polystyrene resin-support; stirring the resulting mixture at a temperature of about 25° C. for a period of about 15 to 36 hours, whereupon a peptide-cyclizing reaction occurs to produce a reaction mixture consisting of the insoluble resin-support (having bound thereon substantially all by-products formed in the reaction) suspended in a solution of the corresponding cyclic peptide, selected from the group consisting of cyclo-(L-leu-gly-L-pro-L-phe-L-ala-gly) and cyclo-(L-val-(tos)-L-orn-L-leu-D-phe-L-pro-L-val-(tos)-L-orn-L-leu-D-phe-L-pro), substantially free of said by-product impurities; separating the insoluble resin-support from the solution of said cyclic peptide; and evaporating this solution to produce the said cyclic peptide in substantially pure form, and in substantially quantitative yield.

* * * * *